US00PP26739P3

(12) United States Plant Patent

Klemm et al.

(10) Patent No.: US PP26,739 P3

(45) Date of Patent: May 17, 2016

(54) *DIANTHUS* PLANT NAMED 'KLEDG13159'

(50) Latin Name: ***Dianthus* sp.**
Varietal Denomination: KLEDG13159

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 105 days.

(21) Appl. No.: 14/120,504

(22) Filed: May 27, 2014

(65) Prior Publication Data

US 2015/0351302 P1 Dec. 3, 2015

(51) Int. Cl.
*A01H 5/02* (2006.01)

(52) U.S. Cl.
USPC ..... Plt./281

(58) Field of Classification Search
USPC ..... Plt./272, 281
See application file for complete search history.

*Primary Examiner* — Susan McCormick Ewoldt

(74) *Attorney, Agent, or Firm* — Barbara Campbell; Bethany R. Roahrig; Cochran Freund & Young, LLC

(57) ABSTRACT

A new *Dianthus* plant particularly distinguished by single-type flowers, raspberry-red flower color, and an upright and bushy plant habit, is disclosed.

1 Drawing Sheet

Genus and species: *Dianthus* sp.
Variety denomination: 'KLEDG13159'.

BACKGROUND OF THE NEW PLANT

The present invention comprises a new and distinct variety of *Dianthus*, botanically known as *Dianthus* sp., and hereinafter referred to by the variety name 'KLEDG13159'. 'KLEDG13159' originated from a cross-pollination between the proprietary female *Dianthus* parent 'DSS 2007 0031' (unpatented) and proprietary male *Dianthus* parent 'DSS 2007 0026' (unpatented) in June 2009 in Stuttgart, Germany.

The seeds from the cross were sown and plants were grown in a greenhouse for evaluation, where an individual plant designated 'KLEDG13159' was selected from the group of plants June 2010 in Stuttgart, Germany. In June 2010, 'KLEDG13159' was first vegetatively propagated by vegetative cuttings. 'KLEDG13159' was found to reproduce true to type in successive generations of asexual propagation in Stuttgart, Germany via vegetative cuttings.

SUMMARY

The following are the most outstanding and distinguishing characteristics of this new variety when grown under normal horticultural practices in Stuttgart, Germany.

1. Single-type flowers having a raspberry-red flower color; and
2. An upright and bushy plant habit.

CROSS-REFERENCE TO RELATED APPLICATIONS

A Plant Breeders Rights application was filed in Canada on Jan. 20, 2014, Application Number 14-8173. 'KLEDG13159' has not been sold or made publicly available more than one year prior to the filing date of the present application.

DESCRIPTION OF THE PHOTOGRAPH

This new *Dianthus* plant is illustrated by the accompanying photograph of a plant approximately 4 to 5-months old and grown in a glass greenhouse in Stuttgart, Germany. The photograph shows the whole plant, including the flowers and foliage and buds and was taken in June 2012 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDG13159'. The data which define these characteristics were collected from asexual reproductions carried out in Stuttgart, Germany. Data was collected on 4-month old plants grown in a greenhouse in March 2014. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Garden carnation.
- *Designation*.—'KLEDG13159'.

Parentage:
- *Female parent*.—The proprietary *Dianthus* variety 'DSS 2007 0031' (unpatented).
- *Male parent*.—The proprietary *Dianthus* variety 'DSS 2007 0026' (unpatented).

Plant:
- *Propagation type*.—Vegetative cuttings.
- *Time to produce a rooted young plant*.—20 days.
- *Root description*.—White, well-branched, and fine.
- *Rooting habit*.—Lanceolate.
- *Plant form*.—Potted and garden plant, upright and bushy.
- *Plant height*.—17.0 cm.
- *Plant diameter or spread*.—17.0 cm.

Lateral branches:

*Length.*—7.0 cm.
*Diameter.*—2.0 cm.
*Internode length.*—1.5 cm.
*Average number of internodes per branch.*—4.
*Branch.*—Is solid.
*Node length.*—0.5 cm.
*Node diameter.*—0.4 cm.
*Texture.*—Smooth.
*Color.*—RHS 139C.

Foliage:

*Arrangement.*—Opposite.
*Length.*—6.0 cm.
*Width.*—0.4 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 139C. Lower surface: RHS 139D.
*Mature leaf color.*—Upper surface: RHS 139C. Lower surface: RHS 139D.
*Venation pattern.*—Pinnate.
*Venation color (both upper and lower surfaces).*—RHS 139C.

Flowers:

*Flower type and habit.*—Most flowers are single, but some flowers are also semi-double.
*Fragrance.*—Present.
*Natural flowering season.*—Spring to fall.
*Flower longevity.*—7 to 9 days.
*Position of the flowers relative to the foliage.*—Far above.
*Buds.*—Length: 1.5 cm. Diameter: 0.5 cm. Shape: Tall cylinder to ovate. Color: RHS 187A. Extrusion of the styles at bud stage: Included in the bud, not visible.
*Corolla.*—Quantity of petals and arrangement: 5 arranged radially. Corolla height: 1.3 cm. Petal length: 3.5 cm. Petal width: 2.0 cm. Petal shape: V-shaped. Petal apex: Obtuse. Petal base: Cuspidate. Petal margin: Serrate. Petal texture (both upper and lower surfaces): Smooth. Petal color: Immature: Upper surface: RHS 68A and RHS 67A. Lower surface: RHS 65B. Mature: Upper surface: RHS 68B and RHS 67A. Lower surface: RHS N66D.
*Calyx.*—Quantity of sepals and arrangement: Composed of 5 sepals. Calyx height: 1.6 cm. Calyx diameter (at the apex): 0.5 cm. Shape of calyx: Cylindrical. Sepal texture (both upper and lower surfaces): Smooth. Sepal color: Upper surface: RHS 187B. Lower surface: RHS 177A.

Peduncles:

*Length.*—14.0 cm.
*Diameter.*—0.2 cm.
*Strength.*—Moderate.
*Texture.*—Smooth.
*Color.*—RHS 138D.

Reproductive organs:

*Stamens.*—Quantity per flower: Greater than 5. Filament length: 1.0 cm. Filament color: RHS 73D. Anther length: 0.2 cm. Anther diameter: 0.08 cm. Anther color: RHS 84D. Pollen amount: Moderate.
*Pistils.*—Quantity per flower: 2. Pistil length: 2.0 cm. Style length: 0.1 cm. Style color: RHS 73D. Stigma shape: Filamentous. Stigma color: RHS 70B. Ovary size: 0.6 cm. Ovary shape: Ovate. Ovary color: RHS 139D.

Fruit and seed set: Seed sometimes observed but additional information on seeds not available.

Disease and pest/insect resistance: No disease and pest/insect resistance observed.

COMPARISON WITH PARENTAL LINES AND KNOWN VARIETY

'KLEDG13159' is a distinct variety of *Dianthus* and is distinguished from its parents as described in Table 1.

TABLE 1

Comparison with Parental Lines

| Characteristic | 'KLEDG13159' | Female Parent 'DSS 2007 0031' | Male Parent 'DSS 2007 0026' |
|---|---|---|---|
| Flower color | Raspberry red | Purple cerise | Pink |
| Flower type | Single | Double | Double |

'KLEDG13159' is a distinct variety of *Dianthus* and is most similar to the commercial *Dianthus* variety 'KLEDG11143' (U.S. Plant Pat. No. 23,150), also commercially known as Everlast™ 'Burgundy Blush'. Differences between the varieties are described in Table 2.

TABLE 2

Comparison with Similar Variety

| Characteristic | 'KLEDG13159' | 'KLEDG11143' |
|---|---|---|
| Flower type | Single | Double |
| Growth | Medium | Compact |

We claim:

1. A new and distinct variety of *Dianthus* plant designated 'KLEDG13159' as illustrated and described herein.

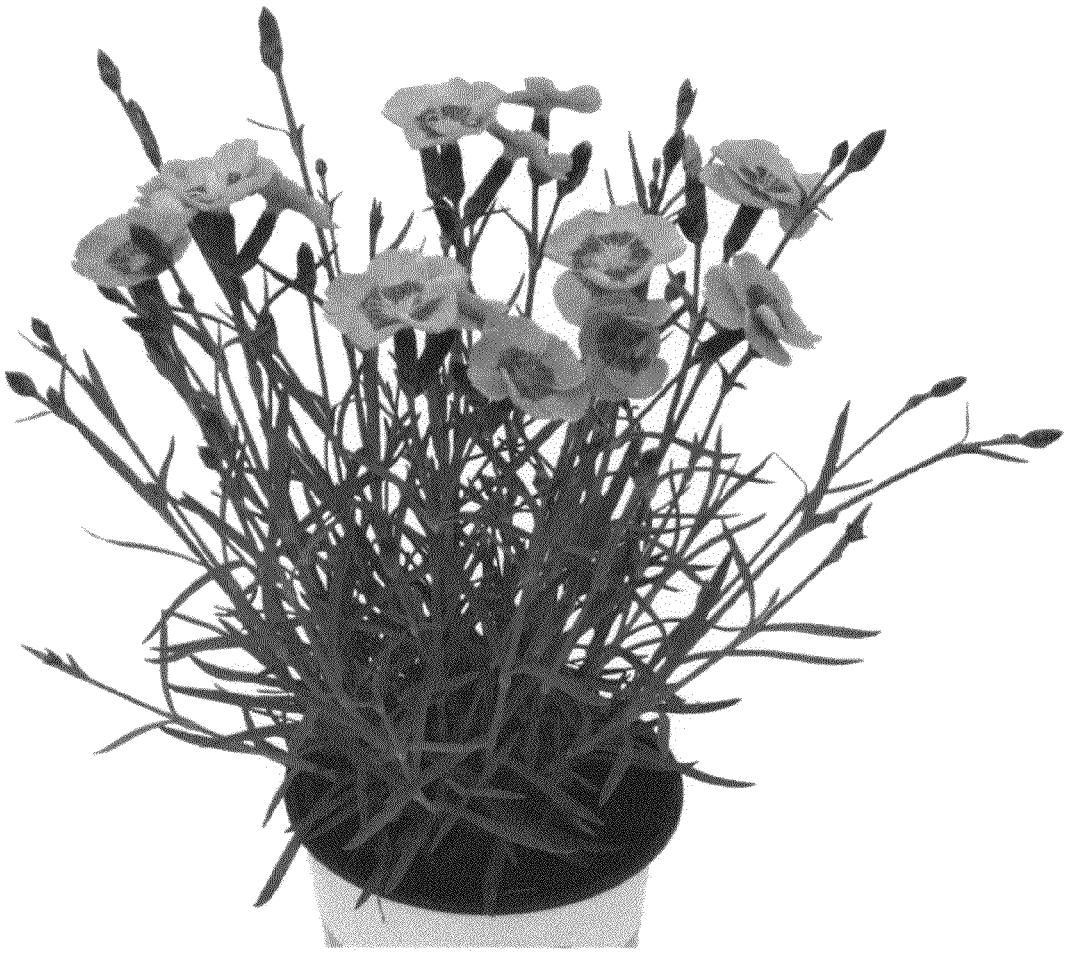

* * * * *